(12) United States Patent
Hedni et al.

(10) Patent No.: US 11,439,651 B2
(45) Date of Patent: Sep. 13, 2022

(54) NASAL SPRAY COMPOSITION FOR COVID-19 AND SARS AND METHOD OF FORMING THE SAME

(71) Applicant: CoFix-RX, LLC, Bloomfield Hills, MI (US)

(72) Inventors: Ravi Hedni, Rochester Hills, MI (US); Karen Raehtz, Troy, MI (US); Dennis G Kaiser, Waterford, MI (US); Andrew Krause, Oxford, MI (US)

(73) Assignee: CoFix-RX, LLC, Bloomfield Hills, MI (US)

( * ) Notice: Subject to any disclaimer, the term of this patent is extended or adjusted under 35 U.S.C. 154(b) by 0 days.

(21) Appl. No.: 17/374,819

(22) Filed: Jul. 13, 2021

(65) Prior Publication Data

US 2022/0117980 A1 Apr. 21, 2022

Related U.S. Application Data

(60) Provisional application No. 63/158,814, filed on Mar. 9, 2021, provisional application No. 63/154,725, filed on Feb. 27, 2021, provisional application No. 63/134,931, filed on Jan. 7, 2021, provisional application No. 63/114,138, filed on Nov. 16, 2020, provisional application No. 63/093,260, filed on Oct. 18, 2020.

(51) Int. Cl.
| | |
|---|---|
| *A61K 31/593* | (2006.01) |
| *A61K 9/00* | (2006.01) |
| *A61K 47/36* | (2006.01) |
| *A61K 47/02* | (2006.01) |
| *A61K 31/592* | (2006.01) |
| *A61K 47/26* | (2006.01) |

(52) U.S. Cl.
CPC .......... *A61K 31/593* (2013.01); *A61K 9/0073* (2013.01); *A61K 31/592* (2013.01); *A61K 47/02* (2013.01); *A61K 47/26* (2013.01); *A61K 47/36* (2013.01)

(58) Field of Classification Search
CPC .. A61K 31/593; A61K 9/0073; A61K 31/592; A61K 47/02; A61K 47/26; A61K 47/36; A61K 9/0043; A61K 31/00; A61P 31/00
See application file for complete search history.

(56) References Cited

U.S. PATENT DOCUMENTS

2014/0243419 A1 * 8/2014 Kurose .................. A61K 47/36
514/675

FOREIGN PATENT DOCUMENTS

CA 2648553 A1 * 11/2007 ............. A61K 47/36

* cited by examiner

*Primary Examiner* — Robert A Wax
*Assistant Examiner* — Quanglong N Truong
(74) *Attorney, Agent, or Firm* — Inventa Capital PLC

(57) ABSTRACT

A nasal spray solution of the present invention includes a Povidone iodine solution; a Vitamin D liquid, Polysorbate 80 nf, Xylitol NF, water sterile, Sodium hydroxide 10% solution, and Polysaccharide 1% solution, wherein 1% solution further includes a gellan gum and a carrageenan, used as carriers to deliver liquids to cells of human and act as entrapment within a polymeric coating to block virus uptake into the cells, inactivate the virus, and protect a lining of an upper respiratory pathways against COVID-19 and SARS.

12 Claims, No Drawings

NASAL SPRAY COMPOSITION FOR COVID-19 AND SARS AND METHOD OF FORMING THE SAME

FIELD OF INVENTION

The present invention relates to a chemical composition for a nasal spray to prevent COVID-19, SARS and other infection and bacteria.

BRIEF DESCRIPTION OF THE BACKGROUND

COVID-19 pandemic stemming from a new strain of coronavirus has had a substantial impact on society and daily life since early 2020. Despite having a seemingly low mortality rate, it is highly contagious and has already caused millions of deaths. COVID-19, ranked as the most severe pandemic in modern time, emerged as a serious public health concern. Due to the lack of effective treatment of COVID-19, accurate and early detection methods to identify COVID-19 serotype are required in order to provide careful patient monitoring and to prevent the disease's progression to a more severe stage.

Researchers have examined pre-existing research into bacterial respiratory tract infections and applied the findings to COVID-19, with some success. According to the scientists, a sphingosine nasal spray could potentially prevent or treat SARS infections. For example, the team from the University of Cincinnati (UC), US, established that sphingosine—a lipid naturally found in the human body, which is key for cellular lipid metabolism—is important in the local immune defenses of epithelial cells, which line the surfaces of the body such as skin, blood vessels, urinary tract and organs and protect them from pathogens.

One of the potential known solutions is Sphingosine. It has been shown in past studies to prevent and eliminate bacterial infections of the respiratory tract, but it is unknown if it can be used to prevent viral infections.

In cultured human cells with SARS particles added sphingosine prevented cellular infection. It was also known that pre-treatment of cultured cells or freshly obtained human nasal epithelial cells with low concentrations of sphingosine prevented adhesion of and infection with the virus.

Transmission of viruses occurs through 4 routes: direct contact, via physical contact with a carrier; indirect contact, interactions with contaminated objects; droplet and airborne transmission, often through coughs, sneezes and breathing; and, aerosolization, atomized virus suspended in airflow.

Airborne transmission of respiratory pathogens, whether through droplets or atomization, is particularly deleterious, with the virus effectively and locally delivered to the respiratory pathways. Recent work, primarily undertaken within the COVID-19 pandemic has heavily focused on providing a deeper understanding on person to person airborne transmission. During the act of coughing, turbulent air forces mucus breakup into droplets (ca. 0.62 to 15.9 μm), which are then expelled through the oronasal passages at flow rates of up to 12 Ls-1, reaching velocities of up to 30 ms-1.

There are many airborne viruses including: influenza-, rhino-, adreno-, entero- and corona-virus. The latter, coronaviridae (CoVs) family, are implicated in a variety of gastrointestinal, central nervous system and respiratory diseases (MERS, SARS); with the latest strain, SARS-CoV-2, receiving much attention due to its devastating impact within the 2020 pandemic. SARS-CoV-2, like all coronaviruses, contains large positive-strand RNA genomes packed within a helical capsid, all housed within a phospholipid bilayer envelope formed on budding. Associated with the viral membrane are 3 main proteins: membrane and envelope proteins, associated with assembly, and spike proteins. The spike proteins, which give rise to its corona shape, are essential for virus survival, mediating entry to the host cell.

Alluding to the above, respired air is primarily routed through the nose. Even though the nasal passages present the highest resistance to airflow, on average ca. 10,000 L of air is inhaled by a healthy human per day. Only once this pathway becomes overloaded does the body switch to respiratory through the mouth. For this reason, the nasal cavity supports two major roles: climate control, creating the correct levels of humidity and air temperature; and, removal of foreign particles including dust, airborne droplets and pathogens. Anatomically, the nose consists of 2 cavities roughly 10 cm in length and half again in height, producing a total surface area of about 150 cm2. Inspired air flows up through the nasal vestibule (nostril) and passes through.

Thus, it is known that sphingosine prevents at least some viral infection by interfering with the interaction of the virus with its receptor; it could be used as a nasal spray to prevent or treat infections with SARS. The nasal spray must be developed, but more research is needed to see if this could be a treatment for COVID-19.

There is always a need for better and improved nasal spray to prevent COVID-19, SARS and other infection and bacteria.

SUMMARY OF THE INVENTION

A nasal spray of the present invention includes a first element such as Povidone iodine solution. The preferred quantity is 12.5 ml. However, it can be less or more than 12.5 ml and the preferred quantity is not intended to limit the scope of the present invention. The nasal spray further includes Vitamin D liquid. The preferred quantity is 1 gram. However, it can be less or more than 1 gram and the preferred quantity is not intended to limit the scope of the present invention. The third element is Polysorbate 80 nf. The preferred quantity is 1 ml. However, it can be less or more than 1 ml and the preferred quantity is not intended to limit the scope of the present invention. The next element is Xylitol NF. The preferred quantity is 5 grams. However, it can be less or more than 1 gram and the preferred quantity is not intended to limit the scope of the present invention. The next element is water sterile. The preferred quantity is 100 ml. However, it can be less or more than 100 ml and the preferred quantity is not intended to limit the scope of the present invention. The other element used is Sodium hydroxide 10% solution. The preferred quantity is 7 GTTS (drops). However, it can be less or more than 7 drops and the preferred quantity is not intended to limit the scope of the present invention 7 GTTS (drops). The final element used is Polysaccharide 1% solution (75:25). The preferred quantity is 20 ml. However, it can be less or more than 20 ml and the preferred quantity is not intended to limit the scope of the present invention.

Airborne pathogens pose high risks in terms of both contraction and transmission within the respiratory pathways, particularly the nasal region. However, there is little in the way of adequate intervention that can protect an individual or prevent further spread.

An advantage of the present invention is to provide spray, known for its mucoadhesive properties, is undertaken and it is characterized for its mechanical, spray distribution, and antiviral properties.

Alluding to the above, our composite mixture containing both the gellan gum and the carrageenan. These two elements are used as carriers (vehicles) for elements to better deliver the liquids to the cells and act as entrapment within a polymeric coating to block virus uptake into the cells, inactivate the virus, and allow clearance within the viscous medium. As such, a fully preventative spray is formulated, targeted at protecting the lining of the upper respiratory pathways against SARS-CoV-2.

These two elements (the gellan gum (0.15 gm) and the carrageenan (0.05 gm)) are used as carriers (vehicles) for Polysaccharide 1% solution to better deliver the liquids to the cells and act as entrapment within a polymeric coating to block virus uptake into the cells, inactivate the virus, and allow clearance within the viscous medium.

Another advantage is to provide the inventive nasal spray targeted at protecting the lining of the upper respiratory pathways against SARS-CoV-2 and other bacteria.

The objects and advantages of the present invention will be more readily apparent from inspection of the following specification, taken in connection with the accompanying drawing, wherein like numerals refer to like parts throughout and in which an embodiment of the present invention is described and illustrated.

The exact manner in which the foregoing and other objects and advantages of the invention are achieved in practice will become more clearly apparent when reference is made to the following detailed description of the preferred embodiments of the invention described in detail in the following specification and shown in the accompanying drawings, where in like reference numbers indicate corresponding parts throughout.

DETAILED DESCRIPTION OF THE INVENTION

For purposes of this patent document, the terms "or" and "and" shall mean "and/or" unless stated otherwise or clearly intended otherwise by the context of their use. The term "a" shall mean "one or more" unless stated otherwise or where the use of "one or more" is clearly inappropriate. The terms "comprise," "comprising," "include," and "including" are interchangeable and not intended to be limiting. For example, the term "including" shall be interpreted to mean "including, but not limited to."

Additionally, as used herein, the singular forms "a," "an," and "the" include plural referents unless the context clearly dictates otherwise. Thus, for example, the term "module" is intended to mean one or more modules or a combination of modules. Furthermore, as used herein, the term "based on" includes based at least in part on. Thus, a feature that is described as based on some cause, can be based only on that cause, or based on that cause and on one or more other causes.

It will be apparent that multiple embodiments of this disclosure may be practiced without some or all of these specific details. In other instances, well-known process operations have not been described in detail in order not to unnecessarily obscure the present embodiments. The following description of embodiments includes references to the accompanying drawing. The drawing shows illustrations in accordance with example embodiments. These example embodiments, which are also referred to herein as "examples," are described in enough detail to enable those skilled in the art to practice the present subject matter. The embodiments can be combined, other embodiments can be utilized, or structural, logical and operational changes can be made without departing from the scope of what is claimed. The following detailed description is, therefore, not to be taken in a limiting sense, and the scope is defined by the appended claims and their equivalents.

A nasal spray of the present invention includes a first element such as Povidone iodine solution. The prefer quantity is 12.5 ml. However, it can be less or more than 12.5 ml and the preferred quantity is not intended to limit the scope of the present invention. The nasal spray further includes Vitamin D liquid. The preferred quantity is 1 gram. However, it can be less or more than 1 gram and the preferred quantity is not intended to limit the scope of the present invention. The third element is Polysorbate 80 nf. The preferred quantity is 1 ml. However, it can be less or more than 1 ml and the preferred quantity is not intended to limit the scope of the present invention. The next element is Xylitol NF. The preferred quantity is 5 grams. However, it can be less or more than 1 gram and the preferred quantity is not intended to limit the scope of the present invention.

The next element is water sterile. The preferred quantity is 100 ml. However, it can be less or more than 100 ml and the preferred quantity is not intended to limit the scope of the present invention. The other element used is Sodium hydroxide 10% solution. The preferred quantity is 7 GTTS (drops). However, it can be less or more than 7 drops and the preferred quantity is not intended to limit the scope of the present invention 7 GTTS (drops). The final element used is Polysaccharide 1% solution (75:25). The preferred quantity is 20 ml. However, it can be less or more than 20 ml and the preferred quantity is not intended to limit the scope of the present invention.

Polysaccharide 1% solution (75:25) includes a gellan gum (25%) and a carrageenan (75%). Alternatively it can be the other way around such as the gellan gum (75%) and the carrageenan will be used in 0.05 grams. Why are we adding the gellan gum and the carrageenan? Airborne pathogens pose high risks in terms of both contraction and transmission within the respiratory pathways, particularly the nasal region.

However, there is little in the way of adequate intervention that can protect an individual or prevent further spread. Our invention is a spray, known for its mucoadhesive properties, is undertaken and it is characterized for its mechanical, spray distribution, and antiviral properties. Our composite mixture containing both the gellan gum and the carrageenan. These two elements are used as carriers (vehicles) for elements to better deliver the liquids to the cells and act as entrapment within a polymeric coating to block virus uptake into the cells, inactivate the virus, and allow clearance within the viscous medium. As such, a fully preventative spray is formulated, targeted at protecting the lining of the upper respiratory pathways against SARS-CoV-2.

Alluding to the above, Povidone-Iodine is an iodophor solution containing a water-soluble complex of iodine and polyvinylpyrrolidone (PVP) with broad microbicidal activity. Iodophors are solutions that contain iodine and a solubilizing agent. In this way, a small amount of iodine is slowly released in solution. They are typically used at concentrations ranging from 6 to 75 ppm. Iodophors penetrate the cell walls and membranes of microorganisms and interfere with DNA synthesis. Free iodine, slowly liberated from the polyvinylpyrrolidone iodine (PVPI) complex in solution, kills eukaryotic or prokaryotic cells through iodination of lipids and oxidation of cytoplasmic and membrane compounds. This agent exhibits a broad range of microbicidal activity against bacteria, fungi, protozoa, and viruses.

Slow release of iodine from the PVPI complex in solution minimizes iodine toxicity towards mammalian cells.

Polysorbates are a class of emulsifiers used in some pharmaceuticals and food preparation. They are often used in cosmetics to solubilize essential oils into water-based products. Polysorbates are oily liquids derived from ethoxylated sorbitan (a derivative of sorbitol) esterified with fatty acids. Common brand names for polysorbates include Kolliphor, Scattics, Alkest, Canarcel, and Tween.

Polysorbate 80 is derived from polyethoxylated sorbitan and oleic acid. The hydrophilic groups in this compound are polyethers also known as polyoxyethylene groups, which are polymers of ethylene oxide. In the nomenclature of polysorbates, the numeric designation following polysorbate refers to the lipophilic group, in this case, the oleic acid.

The full chemical names for polysorbate 80 are: Polyoxyethylene (20) sorbitan monooleate (x)-sorbitan mono-9-octadecenoate poly(oxy-1,2-ethanediyl). The critical micelle concentration of polysorbate 80 in pure water is reported as 0.012 mM. Xylitol is a chemical compound with the formula $C5H12O5$, or $HO(CH2)(CHOH)3(CH2)OH$; specifically, one particular stereoisomer with that structural formula. It is a colorless or white crystalline solid that is soluble in water. It can be classified as a polyalcohol and a sugar alcohol, specifically an alditol.

Xylitol is used as a food additive and sugar substitute. Its European Union code number is E967. Replacing sugar with xylitol in food products may promote better dental health, but evidence is lacking on whether xylitol itself prevents dental cavities.

Sodium hydroxide, also known as lye and caustic soda, is an inorganic compound with the formula NaOH. It is a white solid ionic compound consisting of sodium cations Na+ and hydroxide anions OH. Sodium hydroxide is a highly caustic base and alkali that decomposes proteins at ordinary ambient temperatures and may cause severe chemical burns. It is highly soluble in water, and readily absorbs moisture and carbon dioxide from the air. It forms a series of hydrates $NaOH.nH2O$. The monohydrate $NaOH.H2O$ crystallizes from water solutions between 12.3 and 61.8° C. The commercially available "sodium hydroxide" is often this monohydrate, and published data may refer to it instead of the anhydrous compound.

As one of the simplest hydroxides, sodium hydroxide is frequently utilized alongside neutral water and acidic hydrochloric acid to demonstrate the pH scale to chemistry students.

Polysaccharides or polycarbohydrates, are the most abundant carbohydrate found in food. They are long chain polymeric carbohydrates composed of monosaccharide units bound together by glycosidic linkages. This carbohydrate can react with water (hydrolysis) using amylase enzymes as catalyst, which produces constituent sugars (monosaccharides, or oligosaccharides). They range in structure from linear to highly branched. Examples include storage polysaccharides such as starch, glycogen and galactogen and structural polysaccharides such as cellulose and chitin.

Polysaccharides are often quite heterogeneous, containing slight modifications of the repeating unit. Depending on the structure, these macromolecules can have distinct properties from their monosaccharide building blocks. They may be amorphous or even insoluble in water. When all the monosaccharides in a polysaccharide are the same type, the polysaccharide is called a homopolysaccharide or homoglycan, but when more than one type of monosaccharide is present, they are called heteropolysaccharides or heteroglycans.

Natural saccharides are generally composed of simple carbohydrates called monosaccharides with general formula (CH2O), where n is three or more. Examples of monosaccharides are glucose, fructose, and glyceraldehyde. Polysaccharides, meanwhile, have a general formula of $Cx(H2O)y$ where x is usually a large number between 200 and 2500. When the repeating units in the polymer backbone are six-carbon monosaccharides, as is often the case, the general formula simplifies to (C6H10O5), where typically $40 \leq n \leq 3000$.

As a rule of thumb, polysaccharides contain more than ten monosaccharide units, whereas oligosaccharides contain three to ten monosaccharide units; but the precise cutoff varies somewhat according to convention. Polysaccharides are an important class of biological polymers. Their function in living organisms is usually either structure- or storage-related. Starch (a polymer of glucose) is used as a storage polysaccharide in plants, being found in the form of both amylose and the branched amylopectin. In animals, the structurally similar glucose polymer is the more densely branched glycogen, sometimes called "animal starch". Glycogen's properties allow it to be metabolized more quickly, which suits the active lives of moving animals. In bacteria, they play an important role in bacterial multicellularity.

Cellulose and chitin are examples of structural polysaccharides. Cellulose is used in the cell walls of plants and other organisms and is said to be the most abundant organic molecule on Earth. It has many uses such as a significant role in the paper and textile industries, and is used as a feedstock for the production of rayon (via the viscose process), cellulose acetate, celluloid, and nitrocellulose. Chitin has a similar structure, but has nitrogen-containing side branches, increasing its strength. It is found in arthropod exoskeletons and in the cell walls of some fungi. It also has multiple uses, including surgical threads. Polysaccharides also include callose or laminarin, chrysolaminarin, xylan, arabinoxylan, mannan, fucoidan and galactomannan.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof.

Therefore, it is intended that the invention not be limited to the particular embodiment disclosed as the best mode contemplated for carrying out this invention. It will be apparent that multiple embodiments of this disclosure may be practiced without some or all of these specific details. In other instances, well-known process operations have not been described in detail in order not to unnecessarily obscure the present embodiments.

What is claimed is:

1. A liquid nasal spray composition to treat a viral respiratory infectious disease, the nasal spray composition comprising:
   a first component comprising an iodophor solution that includes iodine and povidone;
   a second component comprising a liquid form of Vitamin D;
   a third component comprising Polysorbate 80 nf;
   a fourth component comprising Xylitol NF;
   a fifth component comprising sterile water;
   a sixth component comprising a 10% solution of sodium hydroxide; and a seventh component comprising a 1% solution of Polysaccharide; the 1% solution of Polysaccharide including a gellan gum and a carrageenan;

wherein the first, second, third, fourth, sixth and seventh components are added and dissolved in the fifth component to produce the liquid nasal spray composition.

2. The liquid nasal spray composition of claim 1, wherein the first component is a Povidone-iodine solution, wherein at least 12.5 ml of the Povidone-iodine solution is used to produce the liquid nasal spray composition.

3. The liquid nasal spray composition of claim 1, wherein at least 1 gm of the liquid form of Vitamin D is used to produce the liquid nasal spray composition.

4. The liquid nasal spray composition of claim 3, wherein at least 1 ml of the Polysorbate 80 nf is used to produce the liquid nasal spray composition.

5. The liquid nasal spray composition of claim 1, wherein at least 5 gm of the Xylitol NF is used to produce the liquid nasal spray composition.

6. The liquid nasal spray composition of claim 1, wherein at least 7 GTTs (drops) of the 10% solution of sodium hydroxide are used to produce the liquid nasal spray composition.

7. The liquid nasal spray composition of claim 1, wherein at least 20 ml of the 1% solution of Polysaccharide are used to produce the liquid nasal spray composition.

8. The liquid nasal spray composition of claim 7, wherein 0.15 gm of the gellan gum and 0.05 gm of the carrageenan are used to produce the 1% solution of Polysaccharide.

9. The liquid nasal spray composition of claim 7, wherein 0.05 gm of the gellan gum and 0.15 gm of the carrageenan are used to produce the 1% solution of Polysaccharide.

10. A liquid nasal spray composition to treat a viral respiratory infectious disease, the nasal spray composition comprising:

a first component comprising an iodophor solution in an amount of 12.5 ml, wherein the iodophor solution includes iodine and povidone;

a second component comprising a liquid form of Vitamin D in an amount of 1 gram;

a third component comprising Polysorbate 80 nf in an amount of 1 ml;

a fourth component comprising Xylitol NF in an amount of 5 grams;

a fifth component comprising sterile water in an amount of 100 ml;

a sixth component comprising a 10% solution of sodium hydroxide in an amount of 7 GTTs (drops); and a seventh component comprising a 1% solution of Polysaccharide in an amount of 20 ml, wherein the 1% solution of Polysaccharide includes a gellan gum and a carrageenan;

wherein the first, second, third, fourth, sixth and seventh components are added and dissolved in the fifth component to produce the liquid nasal spray composition.

11. The liquid nasal spray composition of claim 10, wherein 0.15 grams of the gellan gum and 0.05 gm of the carrageenan are used to produce the 1% solution of Polysaccharide.

12. The liquid nasal spray composition of claim 10, wherein 0.05 grams of the gellan gum and 0.15 gm of the carrageenan are used to produce the 1% solution of Polysaccharide.

* * * * *